(12) United States Patent
Kellerman et al.

(10) Patent No.: US 11,950,828 B2
(45) Date of Patent: Apr. 9, 2024

(54) INTRAVASCULAR ARTERIAL TO VENOUS ANASTOMOSIS AND TISSUE WELDING CATHETER

(71) Applicant: Avenu Medical, Inc., San Juan Capistrano, CA (US)

(72) Inventors: Brad M. Kellerman, Escondido, CA (US); David Trottingwolf Aldridge, Laguna Hills, CA (US); David K. Wrolstad, Escondido, CA (US); Mark A. Ritchart, Dana Point, CA (US); Jeffrey E. Hull, Midlothian, VA (US); Gene Reu, San Juan Capistrano, CA (US)

(73) Assignee: AVENU MEDICAL, INC., San Juan Capistrano, CA (US)

( * ) Notice: Subject to any disclaimer, the term of this patent is extended or adjusted under 35 U.S.C. 154(b) by 352 days.

(21) Appl. No.: 17/451,646

(22) Filed: Oct. 20, 2021

(65) Prior Publication Data

US 2022/0039854 A1 Feb. 10, 2022

Related U.S. Application Data

(60) Division of application No. 16/279,923, filed on Feb. 19, 2019, now Pat. No. 11,172,976, which is a
(Continued)

(51) Int. Cl.
*A61B 18/08* (2006.01)
*A61B 17/11* (2006.01)
(Continued)

(52) U.S. Cl.
CPC ............ *A61B 18/082* (2013.01); *A61B 17/11* (2013.01); *A61B 18/04* (2013.01);
(Continued)

(58) Field of Classification Search
CPC ... A61B 18/04; A61B 18/082; A61B 18/1492; A61B 17/11; A61B 2017/1125; A61B 2018/00404
See application file for complete search history.

(56) References Cited

U.S. PATENT DOCUMENTS

| 4,772,283 A | 9/1988 | White |
| 5,290,278 A | 3/1994 | Anderson |

(Continued)

FOREIGN PATENT DOCUMENTS

| CA | 2626282 | 9/2008 |
| CA | 2498452 | 11/2013 |

(Continued)

OTHER PUBLICATIONS

International Search Report and Written Opinion dated Jun. 12, 2013, corresponding to PCT/US2013/025441, International filing date Feb. 8, 2013.

(Continued)

*Primary Examiner* — Christopher A Flory
(74) *Attorney, Agent, or Firm* — Stinson LLP (57) ABSTRACT

A method of creating an AV fistula between adjacent first and second vessels includes inserting a guidewire from the first vessel into the second vessel. Inserting a catheter including a proximal member and a distal member over the guidewire such that a distal tip of the distal member comes into contact with a selected anastomosis site. Moving the distal member and the proximal member together to clamp tissue surrounding the aperture between the distal face of the proximal member and a proximal face on the distal member. Applying energy to an active heating member on the proximal member to cut and form the aperture, and to weld the edges thereof in order to create a desired fistula between the two vessels. Using a passive heating member disposed on
(Continued)

the distal member to create a heating gradient across a tissue contacting surface of the distal member.

10 Claims, 7 Drawing Sheets

Related U.S. Application Data continuation of application No. 15/295,781, filed on Oct. 17, 2016, now Pat. No. 10,231,771, which is a division of application No. 13/763,501, filed on Feb. 8, 2013, now Pat. No. 9,474,562.

(60) Provisional application No. 61/596,670, filed on Feb. 8, 2012.

(51) Int. Cl.
*A61B 18/00* (2006.01)
*A61B 18/04* (2006.01)
*A61B 18/14* (2006.01)

(52) U.S. Cl.
CPC ... *A61B 18/1492* (2013.01); *A61B 2017/1107* (2013.01); *A61B 2017/1125* (2013.01); *A61B 2017/1139* (2013.01); *A61B 2018/00095* (2013.01); *A61B 2018/0013* (2013.01); *A61B 2018/00184* (2013.01); *A61B 2018/00404* (2013.01); *A61B 2018/00601* (2013.01); *A61B 2018/00619* (2013.01)

(56) References Cited

U.S. PATENT DOCUMENTS

| | | |
|---|---|---|
| 5,425,731 A | 6/1995 | Daniel et al. |
| 5,553,624 A | 9/1996 | Francese et al. |
| 5,830,222 A | 11/1998 | Makower |
| 5,830,224 A | 11/1998 | Cohn et al. |
| 6,024,739 A | 2/2000 | Ponzi et al. |
| 6,068,637 A | 5/2000 | Popov et al. |
| 6,068,638 A | 5/2000 | Makower |
| 6,071,292 A | 6/2000 | Makower et al. |
| 6,083,223 A | 7/2000 | Baker |
| 6,099,542 A | 8/2000 | Cohn et al. |
| 6,190,353 B1 | 2/2001 | Makower et al. |
| 6,235,027 B1 | 5/2001 | Herzon |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,379,319 B1 | 4/2002 | Garibotto et al. |
| 6,398,797 B2 | 6/2002 | Bombard et al. |
| 6,409,721 B1 | 6/2002 | Wheelock et al. |
| 6,464,665 B1 | 10/2002 | Heuser |
| 6,533,778 B2 | 3/2003 | Herzon |
| 6,541,028 B1 | 4/2003 | Kuri-Harcuch et al. |
| 6,561,998 B1 | 5/2003 | Roth et al. |
| 6,579,311 B1 | 6/2003 | Makower |
| 6,613,081 B2 | 9/2003 | Kim et al. |
| 6,616,675 B1 | 9/2003 | Evard et al. |
| 6,626,901 B1 | 9/2003 | Treat |
| 6,669,709 B1 | 12/2003 | Cohn et al. |
| 6,699,245 B2 | 3/2004 | Dinger et al. |
| 6,709,444 B1 | 3/2004 | Makower |
| 6,726,677 B1 | 4/2004 | Flaherty et al. |
| 6,863,684 B2 | 3/2005 | Kim et al. |
| 6,908,463 B2 | 6/2005 | Treat et al. |
| 6,929,009 B2 | 8/2005 | Makower et al. |
| 7,056,325 B1 | 6/2006 | Makower et al. |
| 7,074,220 B2 | 7/2006 | Hill et al. |
| 7,159,592 B1 | 1/2007 | Makower et al. |
| 7,191,015 B2 | 3/2007 | Lamson et al. |
| 7,211,079 B2 | 5/2007 | Treat |
| 7,316,655 B2 | 1/2008 | Garibotto et al. |
| 7,351,247 B2 | 4/2008 | Kupiecki et al. |
| 7,387,636 B2 | 6/2008 | Cohn et al. |
| 7,588,566 B2 | 9/2009 | Treat et al. |
| 7,729,738 B2 | 6/2010 | Flaherty et al. |
| 7,846,172 B2 | 12/2010 | Makower |
| 7,988,690 B2 | 8/2011 | Chanduszko et al. |
| 8,236,014 B2 | 8/2012 | Breneman et al. |
| 8,721,639 B2 | 5/2014 | Mirizzi et al. |
| 8,834,518 B2 | 9/2014 | Faller et al. |
| 9,138,230 B1 | 9/2015 | Buelna |
| 9,439,728 B2 | 9/2016 | Hull et al. |
| 9,445,868 B2 | 9/2016 | Hull et al. |
| 9,452,015 B2 | 9/2016 | Kellerman et al. |
| 9,474,562 B2 | 10/2016 | Kellerman et al. |
| 9,522,016 B2 | 12/2016 | Kellerman et al. |
| 9,649,157 B1 | 5/2017 | Buelna |
| 2002/0095152 A1 | 7/2002 | Ciarrocca et al. |
| 2002/0188294 A1 | 12/2002 | Couture et al. |
| 2003/0040764 A1 | 2/2003 | Adams |
| 2003/0129382 A1 | 7/2003 | Treat |
| 2003/0171747 A1 | 9/2003 | Kanehira et al. |
| 2003/0225426 A1 | 12/2003 | Hill et al. |
| 2003/0229344 A1 | 12/2003 | Dycus et al. |
| 2004/0073238 A1 | 4/2004 | Makower |
| 2004/0078035 A1 | 4/2004 | Kanehira et al. |
| 2004/0176756 A1 | 9/2004 | McGaffigan |
| 2004/0204725 A1 | 10/2004 | Bayer |
| 2005/0033329 A1 | 2/2005 | Bombard et al. |
| 2005/0033330 A1 | 2/2005 | Vargas et al. |
| 2005/0033420 A1 | 2/2005 | Christie et al. |
| 2005/0038457 A1 | 2/2005 | Vargas et al. |
| 2005/0107775 A1 | 5/2005 | Huang et al. |
| 2005/0131402 A1 | 6/2005 | Ciarrocca et al. |
| 2005/0251167 A1 | 11/2005 | Voegele et al. |
| 2006/0020265 A1 | 1/2006 | Ryan |
| 2006/0111704 A1 | 5/2006 | Brenneman et al. |
| 2006/0122592 A1 | 6/2006 | Treat |
| 2006/0142788 A1 | 6/2006 | Wilson et al. |
| 2006/0189979 A1 | 8/2006 | Esch et al. |
| 2006/0217706 A1 | 9/2006 | Lau et al. |
| 2006/0259073 A1 | 11/2006 | Miyamoto et al. |
| 2007/0175963 A1 | 8/2007 | Bilotti et al. |
| 2007/0276363 A1 | 11/2007 | Patton et al. |
| 2008/0045942 A1 | 2/2008 | Truckai et al. |
| 2008/0187989 A1 | 8/2008 | McGreevy et al. |
| 2009/0048589 A1 | 2/2009 | Takashino et al. |
| 2009/0069807 A1 | 3/2009 | Eggers et al. |
| 2009/0275876 A1 | 11/2009 | Brenneman et al. |
| 2009/0312783 A1 | 12/2009 | Whayne et al. |
| 2010/0152723 A1 | 6/2010 | Esch et al. |
| 2011/0011916 A1 | 1/2011 | Levine |
| 2011/0028970 A1 | 2/2011 | Woloszko et al. |
| 2011/0095067 A1 | 4/2011 | Ohdaira |
| 2011/0251608 A1 | 10/2011 | Timm et al. |
| 2011/0251609 A1 | 10/2011 | Johnson et al. |
| 2011/0276045 A1 | 11/2011 | Truckai et al. |
| 2011/0282341 A1 | 11/2011 | Carmel et al. |
| 2011/0288546 A1 | 11/2011 | Abbott et al. |
| 2011/0306959 A1 | 12/2011 | Kellerman et al. |
| 2011/0306993 A1 | 12/2011 | Hull et al. |
| 2012/0059289 A1 | 3/2012 | Nield et al. |
| 2012/0078246 A1 | 3/2012 | Mirizzi et al. |
| 2012/0302935 A1 | 11/2012 | Miller et al. |
| 2012/0316550 A1 | 12/2012 | Lau et al. |
| 2013/0281998 A1 | 10/2013 | Kellerman et al. |
| 2014/0142561 A1 | 5/2014 | Reu et al. |
| 2015/0164505 A1 | 6/2015 | Brenneman et al. |
| 2016/0235410 A1 | 8/2016 | Kellerman et al. |
| 2017/0007311 A1 | 1/2017 | Hull et al. |
| 2017/0086904 A1 | 3/2017 | Reu et al. |

FOREIGN PATENT DOCUMENTS

| | | |
|---|---|---|
| CA | 2804525 | 9/2018 |
| EP | 2263586 | 6/2018 |
| JP | 2003-506190 | 2/2003 |
| WO | WO112090 | 2/2001 |
| WO | WO2011159825 | 12/2011 |
| WO | WO2012068273 | 5/2012 |

(56) References Cited

FOREIGN PATENT DOCUMENTS

OTHER PUBLICATIONS

International Preliminary Report on Patentability dated May 29, 2014, corresponding to PCT/US2013/025441, International filing date Feb. 8, 2013.
Office Action for corresponding Japanese App. No. 2014-556754, dated Jan. 11, 2017.
Examination Report for corresponding Canadian Patent App. No. 2863248, dated Sep. 24, 2019.

INTRAVASCULAR ARTERIAL TO VENOUS ANASTOMOSIS AND TISSUE WELDING CATHETER

STATEMENT OF RELATED CASES

This application is a divisional application under 35 U.S.C. 120 of commonly assigned U.S. patent application Ser. No. 16/279,923, entitled Intravascular Arterial to Venous Anastomosis and Tissue Welding Catheter, filed on Feb. 19, 2019, which is a continuation application under 35 U.S.C. 120 of commonly assigned U.S. patent application Ser. No. 15/295,781, entitled Intravascular Arterial to Venous Anastomosis and Tissue Welding Catheter, filed on Oct. 17, 2016, now U.S. Pat. No. 10,231,771, which in turn is a divisional application under 35 U.S.C. 120 of commonly assigned U.S. patent application Ser. No. 13/763,501, entitled Intravascular Arterial to Venous Anastomosis and Tissue Welding Catheter, filed on Feb. 8, 2013, now U.S. Pat. No. 9,474,562, which in turn claims the benefit under 35 U.S.C. 119(e) of the filing date of Provisional U.S. Application Ser. No. 61/596,670, entitled Intravascular Arterial to Venous Anastomosis and Tissue Welding Catheter, filed on Feb. 8, 2012, and is also related to U.S. application Ser. No. 13/161,356, entitled Intravascular Arterial to Venous Anastomosis and Tissue Welding Catheter, filed on Jun. 15, 2011, and now issued as U.S. Pat. No. 9,452,015. All of these prior applications are expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact, and to create a leak-free blood flow path between them. The vessels are joined together with suture or clips, in an open surgical procedure. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents. Such procedures are time consuming, clinician dependent (open to surgical error), and often result in strictures, or clotting of the vein or artery.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with catheters placed in large veins, prosthetic grafts attached to an artery and a vein, or a fistula where an artery is attached directly to the vein.

Fistulas for hemodialysis are required by patients with kidney failure. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater. Dialysis fistulas have to be close to the skin (<6 mm), and large enough (>4 mm) to access with a large needle. The fistula needs to be long enough (>6 cm) to allow adequate separation of the access and return needle to prevent recirculation of dialysed and non-dialysed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present disclosed invention eliminates the above described open procedures, reduces operating time, and allows for a consistent and repeatable fistula creation.

It is well known that heat energy, whether its source is Radio Frequency (RF), Direct Current (DC) resistance, or laser, will attach and weld tissue or vessels upon direct pressure and contact over the targeted weld area. This is often done with jaw-type, compression heat delivery devices. It is also well known that radially expandable devices such as balloons, metal cages, and baskets are often coupled with energy in the form of RF or DC resistance, or in the case of balloons, heated saline, and used intraluminally to ablate tissue, stop bleeding, or create a stricture.

The present invention uses catheter based devices that are advanced from one vessel into an adjacent vessel (i.e. a vein into an artery), join the vessel walls by applying heat, and cut through the two walls, creating an anastomosis.

The inventive catheter-based devices track over a guidewire which has been placed from a first vessel, such as a vein, into a second vessel, such as an artery, or more broadly between any other two vascular structures. The distal tip of the catheter has a tapered shape which allows the catheter to advance and dilate easily through the vessel walls. Proximal to the distal tip, the catheter has a significant reduction in diameter, and then a blunt, oval shaped tapered surface. As the catheter is further advanced, the blunt proximal surface comes into contact with the wall of the first vessel and encounters resistance, and cannot perforate through the wall into the second vessel. The distal tip, which has a matching blunt surface on its proximal end, is then retracted, capturing the walls of the two vessels between the two blunt surfaces. A known, controlled pressure (approximately 100 mN/mm$^2$-400 mN/mm$^2$) is applied between the two surfaces. The pressure can be controlled either internally in the catheter or by the handle attached to the proximal end of the catheter. Heat energy is then applied to the blunt surfaces for approximately 1-30 seconds to weld the walls of the two vessels together. It is possible to apply heat energy to only one surface as well. Heat energy can be applied through several different methods, including, but not limited to, RF, DC resistance, inductance, or a combination thereof. The heat energy is controlled at a known temperature ranging from between about 150-300 C. The heat may be applied by applying a steady energy, pulsing energy, incrementing energy, decrementing energy, or a combination thereof.

After coaptation of the vessel walls, the heat is increased to then cut through the vessel walls to create a fistula of the desired size. It should be noted that it is also possible to apply the same heat energy to both weld the vessel walls and to cut through the vessel simultaneously, or to cut through the vessel then weld the vessels' walls together. Alternatively, the same heat energy could be used to weld the vessel walls, followed by a non-energized, mechanically created cut through the vessel walls.

More particularly, there is provided a device for creating an arteriovenous (AV) fistula, which comprises an elongate member, a distal member having a tapered distal end, which is connected to the elongate member and movable relative to the elongate member, and a first heating member disposed on a blunt tapered face of one of the movable distal member and the elongate member. A second heating member is disposed on a blunt tapered face of the other one of the movable distal member and the elongate member. The heating members are adapted to cut through the tissue to create the fistula. The elongate member comprises an elongate outer tube.

A shaft connects the distal member to the elongate member, and is extendable and retractable to extend and retract the distal member relative to the elongate member. One of the shaft and the distal member are fabricated of a flexible material. Preferably, the blunt tapered face on the proximal elongate member comprises a distal tapered face and the blunt tapered face on the distal member comprises a proximal tapered face, wherein the distal tapered face and the proximal tapered face are substantially aligned to one another. The first heating member is disposed on the proximal tapered face and the second heating member is disposed on the distal tapered face. One of the first and second heating members is active, and the other is passive, in some embodiments. The active heating member is energized, preferably by DC resistive energy. The passive heating member comprises a passive heat conductive surface. The active heating member preferably has an oval shape.

In some embodiments, the distal member is tapered and flexible. It may be constructed to be rotatable relative to the elongate member.

Structure for retaining tissue is provided, and associated with one of the heating members. In illustrated embodiments, this structure may comprise a plurality of protruding elements disposed adjacent to a face of at least one of the heating members. At least one of the elongate member and the distal member preferably comprises a cavity for receiving tissue retained by this structure, and this cavity is preferably disposed within and bounded by one of the heating members.

Regarding the aligned proximal and distal tapered faces, a coating, which may be PTFE, is preferably disposed thereon to minimize tissue adhesion. Additionally, in preparation for receiving this coating, each of the proximal and distal tapered faces are constructed to have a smooth surface finish of approximately 25-100 micro inches.

A conductive material is preferably disposed above, below, or within at least one of the heating members, for spreading heat generated by the heating member and creating a temperature gradient emanating outwardly from the heating member throughout the area of blunt tapered surface on which it is disposed.

In another aspect of the invention, there is disclosed a method of creating an AV fistula between adjacent first and second vessels, which comprises a step of inserting a guidewire from the first vessel into the second vessel, inserting a catheter comprising a proximal elongate member and a distal member over the guidewire, so that a tapered distal tip of the distal member comes into contact with a selected anastomosis site, and advancing the distal member into the second vessel, until a blunt tapered distal face of the elongate member contacts a tissue wall of the first vessel, so that the elongate member remains in the first vessel, thereby enlarging an aperture between the two vessels. A further step involves moving the distal member and the elongate member together to clamp tissue surrounding the aperture between the blunt tapered distal face of the elongate member and a corresponding blunt tapered proximal face on the distal member, and applying energy to a heating member on one of the distal member and the elongate member to cut and form the aperture, and to weld the edges thereof in order to create a desired fistula between the two vessels.

Preferably, during the applying energy step, a temperature of 150-300° C. is maintained at the location where the aperture is being cut. The moving and clamping step further preferably comprises applying a known, controlled pressure between the blunt tapered distal face on the elongate member and a corresponding blunt tapered proximal face on the distal member, wherein the known, controlled pressure is within a range of approximately 100 mN/mm$^2$ to 400 mN/mm$^2$.

The method may include a step of rotation the distal member during the advancing step, for a purpose of reducing frictional resistance to the distal member, and may also advantageously further comprise a step of retaining cut tissue using structure associated with the heating member. This structure may include a cavity for receiving the tissue, as well as a plurality of protruding elements extending from at least one of the blunt tapered faces and surrounding the cavity.

The invention, together with additional features and advantages thereof, may best be understood by reference to the following description taken in conjunction with the accompanying illustrative drawings.

DESCRIPTION OF THE PREFERRED EMBODIMENT

Figure 1:
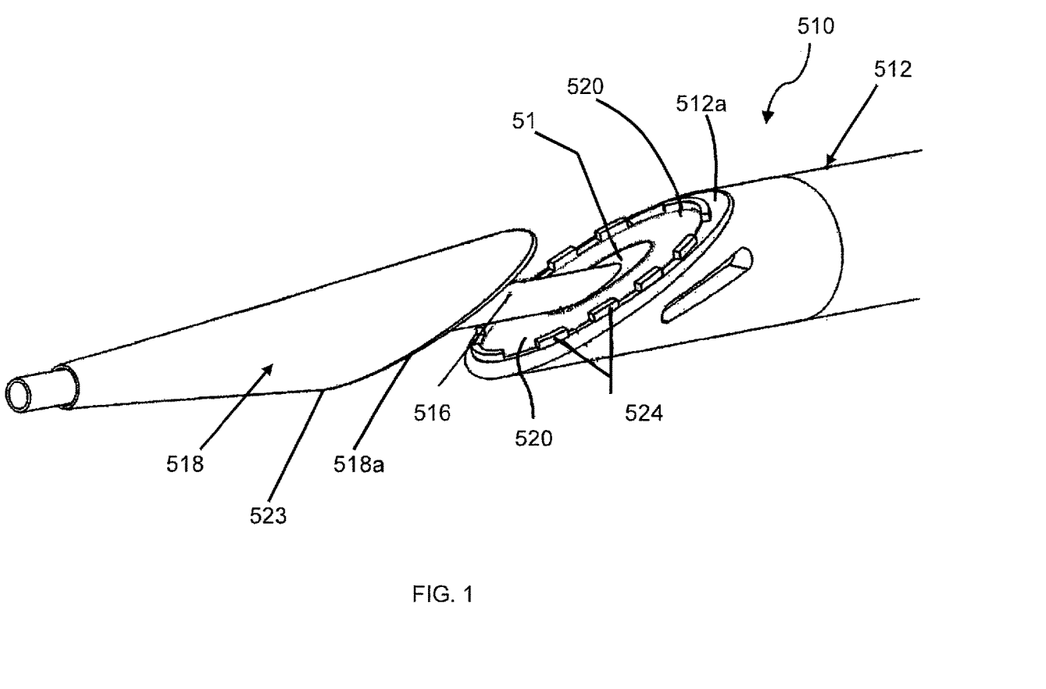
FIG. 1 is an isometric view of an embodiment of a catheter device constructed in accordance with the principles of the present invention.
Figure 11:
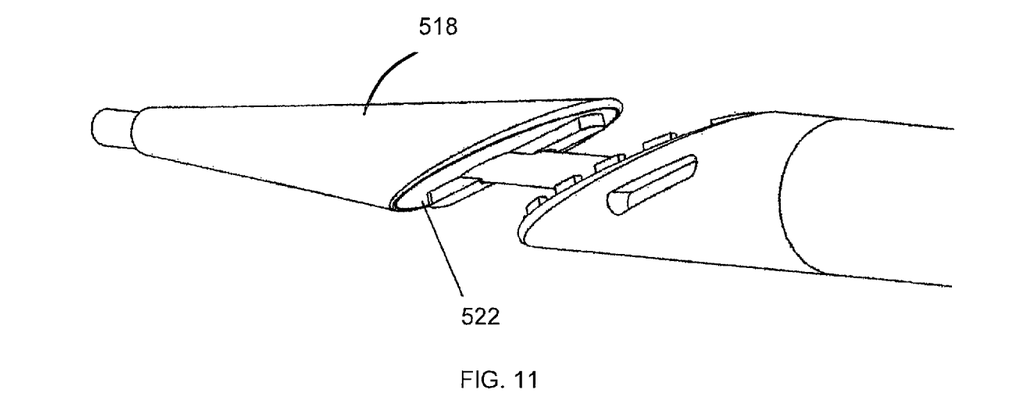
FIG. 11 is an isometric view similar to FIG. 1, illustrating an alternative embodiment of the invention.

Referring now more particularly to the drawings, as illustrated in FIG. 1, a DC resistive heat catheter 510 is shown, which comprises an elongate outer tube 512 having an outer diameter that can range from 3F-12F. It may be manufactured from a variety of materials, either polymeric or metallic. It comprises a central lumen 514, into which a tubular structure 516, which defines its own lumen, disposed on a tip 518, may slidably engage. There are separate lumens that run down the elongated core of the outer tube 512 for wiring heating elements 520, 522 (proximal and distal as shown in FIG. 1 and FIG. 11 respectively), disposed on aligned blunt tapered faces 512a and 518a, respectively, of the respective elongate outer tube 512 and distal tip 518, and to measure the temperature during the coaptation and cutting processes.

In the operation of this configuration, the catheter may be powered using DC resistive energy to the active proximal heat transfer element 520 with the distal heat transfer element 522 acting as a passive heat conductive surface to promote heat transfer through the coapted tissue interface from the active element 520 to the passive element 522. The system can also be used in an alternate configuration wherein element 522 provides the active heat transfer element and element 520 provides the passive heat conductive surface to promote heat transfer through the coapted tissue. Both heating elements 520, 522 may be active, if desired. The heat transfer elements are fabricated with matching angles to increase the surface area of coaptation and fistula size relative to the catheter diameter. These angles can be adjusted to achieve desired fistula sizing. The DC heat transfer elements are conductive on the front opposing faces to maximize energy density. The DC heat transfer elements 520, 522 are oval shaped and are adapted to cut an anastomosis which is larger than the diameter of the shaft 516. There are protruding elements 524 adjacent to the face of proximal heat transfer element 520 to promote tissue retention during welding and cutting. The entire opposing surfaces 512a and 518a of the proximal and distal tip heat transfer elements 520 and 522, respectively, are constructed to have a smooth surface finish of approximately 25-100 micro inches that is treated with a coating such as PTFE to minimize tissue adhesion during or after welding and cutting.

Figure 12:
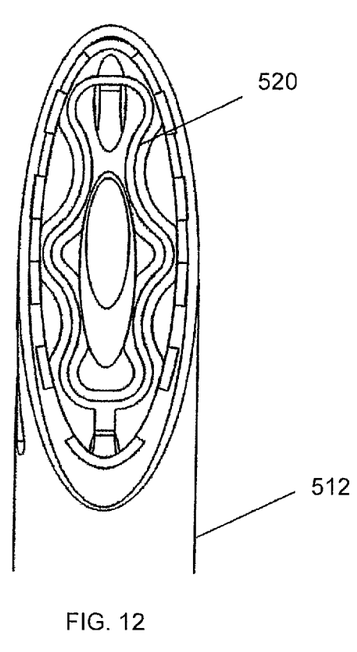
FIG. 12 is an orthogonal view of the proximal active heat transfer element in the embodiment of FIG. 11.

As noted above, FIGS. 11 and 12 are noted as being illustrative of an alternative embodiment. This is because, as shown in FIG. 12, it shows an alternative heating element 520 on the elongate outer tube 12. However, as illustrated, the tip 518, with heating element 522 of each of the embodiments of FIGS. 1 and 11 may be interchangeable or identical.

The apparatus shown and described above in connection with FIGS. 1, 10, 11, and 12 will now be further described in conjunction with an explanation of a particular method by which the system 510 may be used to create an AV fistula. This method is illustrated more particularly in FIGS. 2-9.

Figure 2:
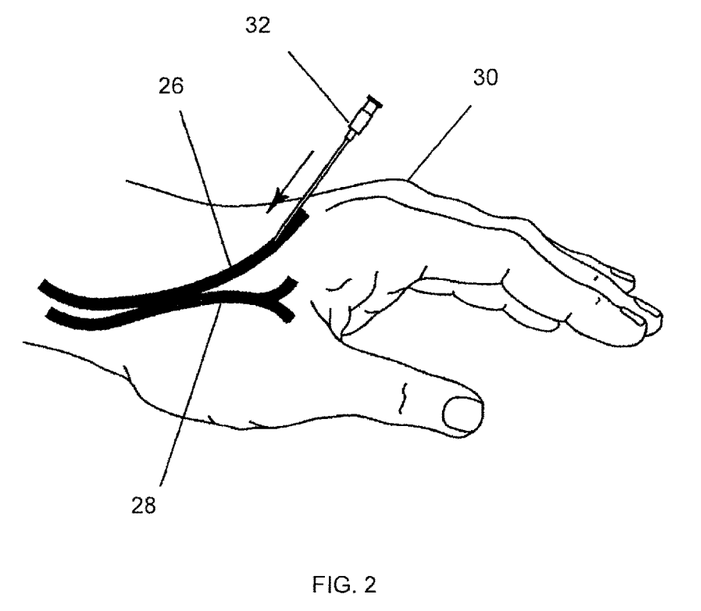
FIG. 2 is a view illustrating a method of access to a first blood vessel in a patient's hand, using a device of the present invention, such as the device illustrated in FIG. 1.
Figure 3:
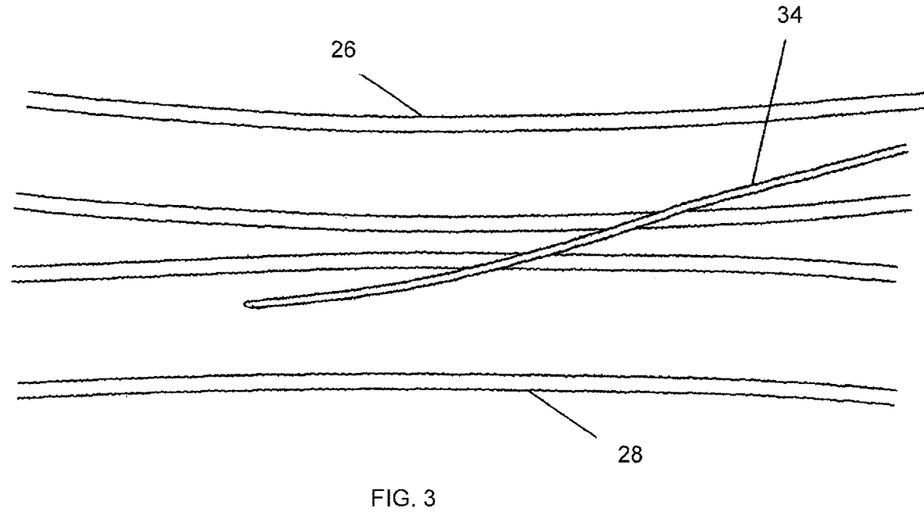
FIG. 3 is a schematic view illustrating the placement of a guidewire from the first blood vessel into a second adjacent blood vessel, in accordance with the present invention.

To begin the inventive method of creating an AV fistula, the practitioner selects an appropriate procedural site having each of a first vessel 26 and a second vessel 28 in close proximity to one another. In currently preferred approaches, the first vessel 26 comprises a vein, and the second vessel 28 comprises an artery, but the invention is not necessarily limited to this arrangement. As illustrated in FIG. 2, one presently preferred location is the hand 30 of a patient. Then, generally employing principles of the Seldinger technique, as shown in FIG. 2, the first vessel 26 is punctured by needle 32, which is inserted therein, for the purpose of introducing an access sheath into the site. Then, using suitable techniques, such as the technique described in Provisional U.S. Application Ser. No. 61/354,903, filed on Jun. 15, 2010 and U.S. application Ser. No. 13/161,182, filed on Jun. 15, 2011, both applications being herein expressly incorporated by reference, in their entirety, a guidewire 34 is inserted into the patient, from the first vessel 26 into the second vessel 28, as shown in FIG. 3.

Figure 4:
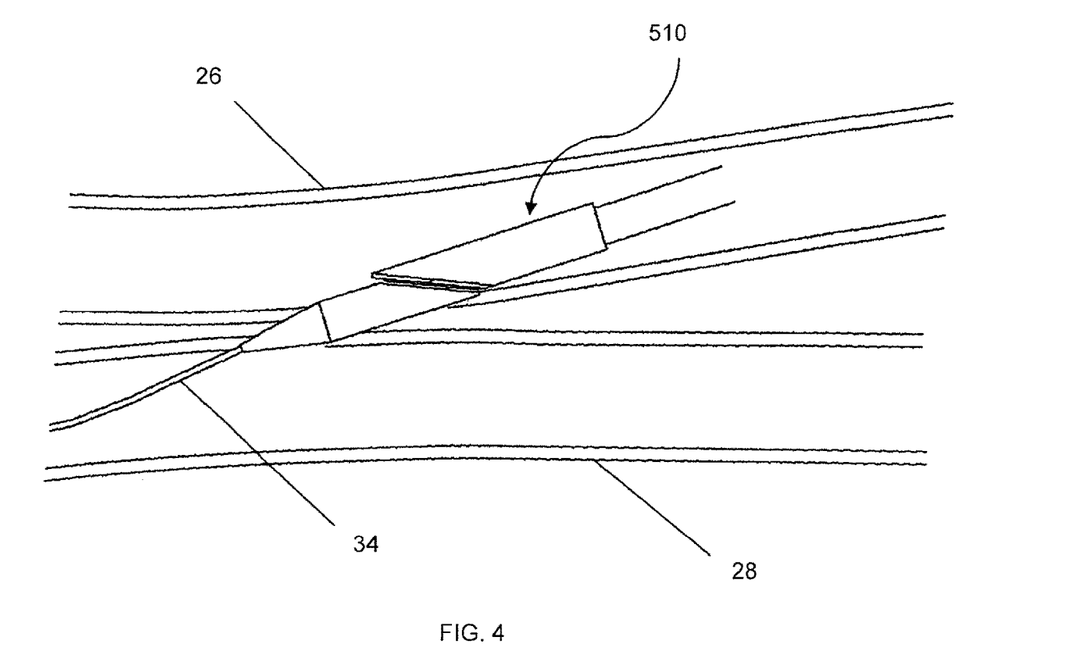
FIG. 4 is a view similar to FIG. 3, wherein the catheter is advanced over the guidewire into the first blood vessel (or vein) with the distal tip entering into the adjacent second vessel (or artery)
Figure 5:
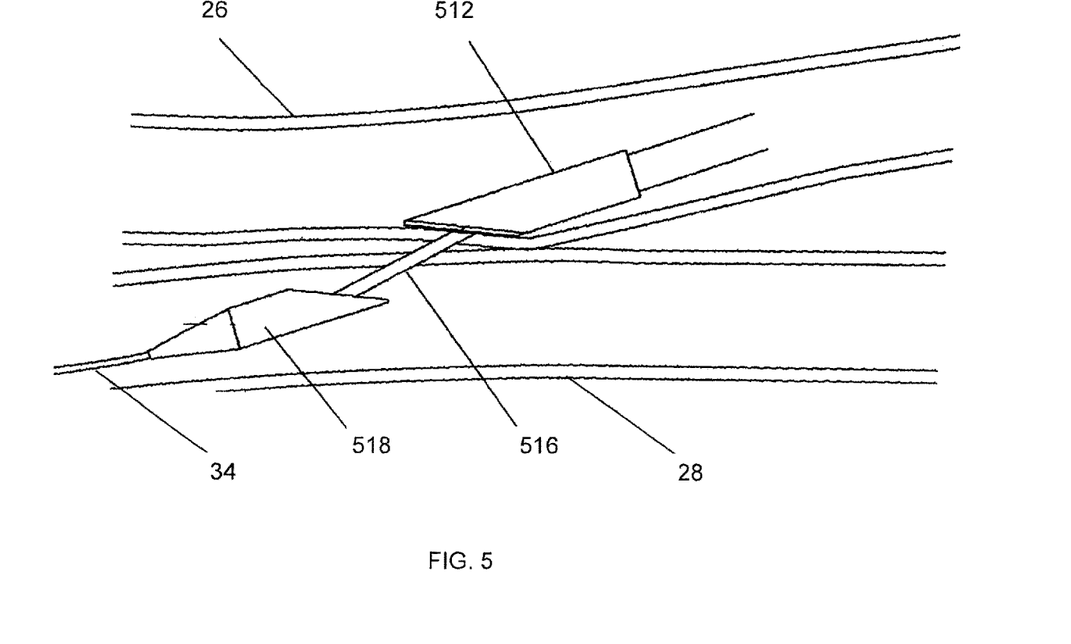
FIG. 5 is a view similar to FIG. 4, wherein the catheter distal tip has been fully extended into the second blood vessel.

The guidewire 34 creates an access path for catheter 510. The catheter 510 is inserted into the patient by loading a proximal end of the guidewire into the lumen 516 of tip 518, which is fabricated to be flexible and tapered. Alternatively, tip 518 could be fabricated to be rigid and attached to a flexible shaft 516. The catheter 510 is advanced further into the patient, tracking over the guidewire 34, until the tapered dilating distal tip 518 comes into contact with the selected anastomosis site. The device 510 can be tracked over the guidewire with the distal tip extended (as shown in FIG. 5) or retracted (as shown in FIG. 4). The distal tip is extended and further advanced into the second vessel 28 (FIG. 5) by advancing the central tubular structure 516 distally from outer tube 512, thereby dilating the opening in the vessel, so that the distal tip 518 is in the second vessel 28, and the outer tube 512 is in the first vessel 26, with its distal tapered surface 512a contacting the inner wall of the first vessel 26. If resistance is felt, tip 518 can be rotated to reduce the friction. Alternatively, the entire system can be rotated to reduce friction. At this juncture, the opening formed in the wall of vessel 26 and 28 has recovered back to a smaller diameter and fits tightly around the shaft 516, as shown.

As noted above, the distal tip 518 of the catheter device has a tapered shape, tapering in the distal direction, which allows the catheter to advance and dilate easily through the vessel walls. Proximal to the tapered end of the distal tip 518, at approximately point 523 (FIG. 1) the catheter has a significant reduction in diameter, because of the formation of the distal tapered end blunt face 518a, proximal to which is the blunt, oval shaped tapered surface 512a of the tube 512. As the catheter is further advanced, the blunt proximal surface 512a comes into contact with the wall of the first vessel 26 and encounters resistance, and cannot perforate through the wall into the second vessel 28.

Figure 6:
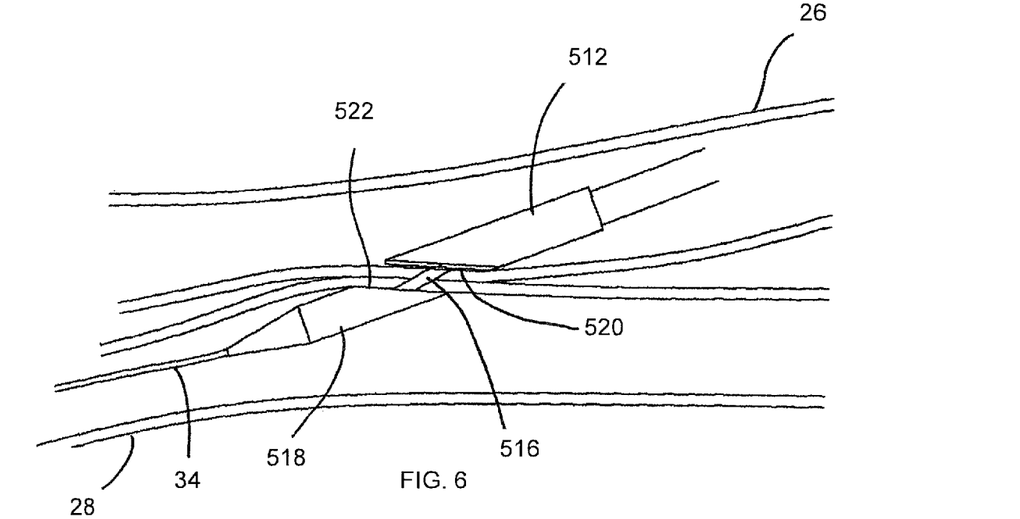
FIG. 6 is a view similar to FIG. 5, wherein the catheter distal tip has been retracted to create coaptation of the first and second blood vessels.
Figure 7:
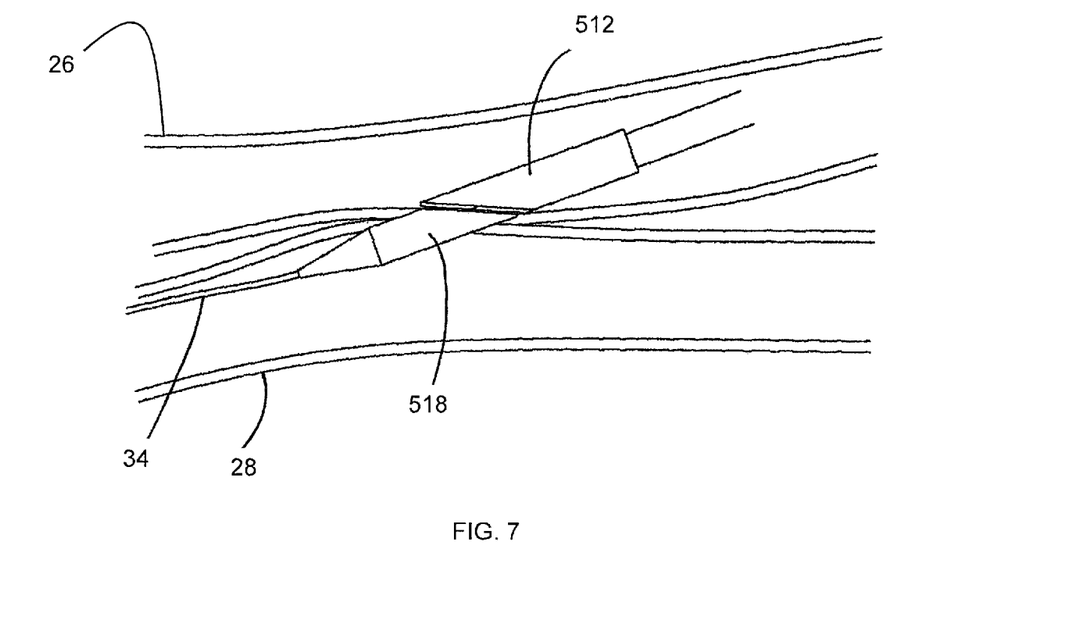
FIG. 7 is a view similar to FIG. 6, wherein heat energy is applied to weld and cut a communicating aperture in the coapted blood vessels.
Figure 8:
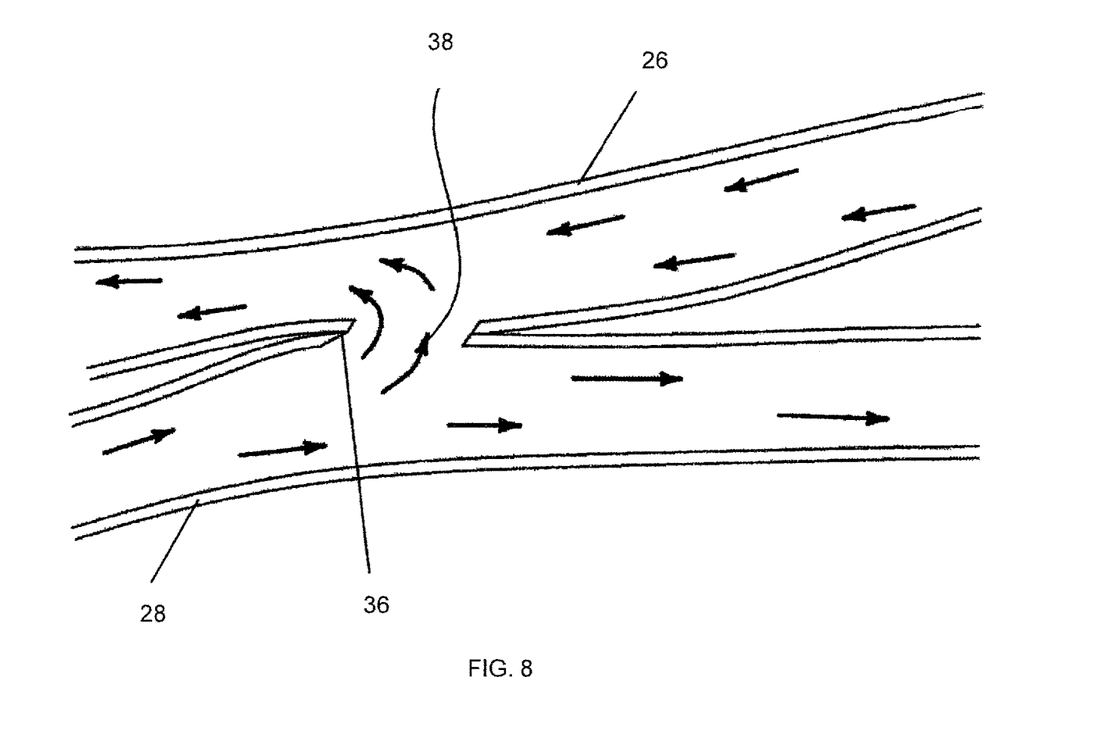
FIG. 8 is a view illustrating in an axial orientation the coapted, welded blood vessels and communicating aperture created by the device and methods of the present invention after the inventive device has been withdrawn from the procedural site.

After the distal tip 518 is advanced into the second vessel 28, as illustrated in FIG. 6, a slight tension, or alternatively a slight pressure, is applied to the distal DC resistive heat element 522 and associated tapered face 518a, to seat them against the vessel 28 wall and promote vessel apposition. The blunt shape of the proximal end 512a of the distal tip 518 prevents the distal tip from inadvertently retracting back through the vessel wall. The proximal end of the device 510, namely outer tube 512, is then advanced to close the spacing between the tube 512 and tip 518, until the walls of the first and second vessels 26 and 28 respectively, are captured between the facing blunt surfaces 512a and 518a, respectively, of each of the outer tube 512 and distal tip 518.

A known, controlled pressure (approximately 100 mN/mm$^2$-400 mN/mm$^2$) is applied between the two surfaces 512a, 518a. The pressure can be controlled either internally in the catheter or by a handle 42 attached to the proximal end of the catheter. At this juncture, with the vessels securely clamped (FIG. 7), heat energy is applied to the blunt surfaces 512a, 518a for approximately 1-30 seconds to weld the walls of the two vessels together. As noted above, it is possible to apply heat energy to only one of the two surfaces as well, with the other surface acting as a passive heat conductor. Heat energy can be applied through several different methods, including, but not limited to, RF, DC resistance, inductance, or a combination thereof. The heat energy is controlled at a known temperature ranging from between about 150-300° C. The heat may be applied by applying a steady energy, pulsing energy, incrementing energy, decrementing energy, or a combination thereof. As the heat elements weld and cut the vessels, the heat elements will move closer to one another. When fully retracted, the system 510 is designed so that the two heat elements 520, 522 come into direct contact with one another to ensure a complete cut and capture of the vessel tissue to be removed. A variety of heat energy profiles may be used to achieve the desired coaptation and cutting. For example, a rapidly stepped or ramped increase to achieve and maintain the aforementioned desired temperature setting of 150° C.-300° C. may be applied to maximize welding prior to cutting. Energy may be modulated based upon the impedance of the tissue or temperature feedback. Different energy application durations, or cyclic pulses may be used to maximize welding and cutting, while minimizing heat transfer to adjacent tissues. The distal end of outer tube 512, in the vicinity of heat element 520, is configured to have insulating properties to minimize heat transfer to adjacent tissues. The active heat element is an oval shape that cuts an anastomosis larger that the diameter of the shaft 516. Within the oval shape of the cutting elements, there is a cavity for capturing the tissue that has been cut. The entire surface of the proximal and distal heat elements is configured to have a non-stick coating, such as PTFE, to limit tissue adhesion.

After coaptation of the vessel walls, the heat is increased to then cut through the vessel walls to create a fistula of the desired size. It should be noted that it is also possible to apply the same heat energy to both weld the vessel walls and to cut through the vessel simultaneously, or to cut through the vessel, then weld the vessel's walls together. Alternatively, the same heat energy may be used to weld the vessel walls, followed by a non-energized, mechanically created cut through the vessel walls.

Figure 9:
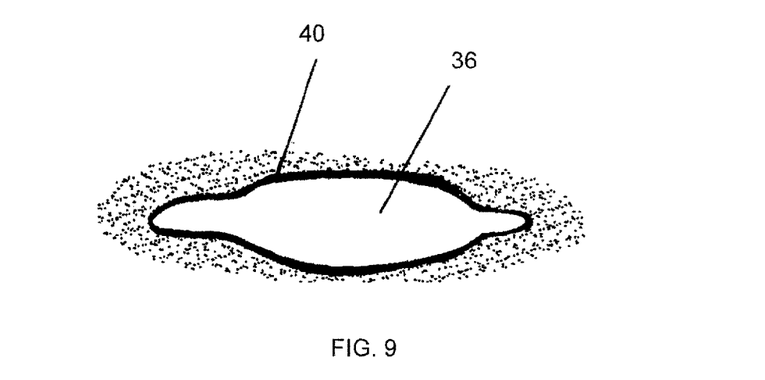
FIG. 9 is a schematic view in an orthogonal orientation relative to FIG. 8, illustrating a detailed view of the welded blood vessels and elongate communicating aperture formed between the two adjacent vessels to create the fistula.

Regarding the tissue welding process, as noted above, more particularly, the DC resistive energy, or other energy source, functions to fuse or weld the vessels together, creating an elongate aperture 36 (FIG. 8) through the opposing walls of each of the first and second vessels, as well as any intervening tissue. As formed, the elongate aperture may typically resemble a slit. However, as pressurized flow 38 begins to occur through aperture 36, which creates a communicating aperture between the first and second blood vessels, the aperture widens in response to the pressure, taking the shape of an ellipse as it opens to form the desired fistula. The effect is illustrated in FIG. 9. The edges 40 of the aperture are cauterized and welded. FIG. 9 illustrates the weld from the venous (first vessel) side. As shown, the cut area corresponds to the shape of the heater wire. It can be of multiple shapes, such as round, oval, a slit, or a combination as shown. The area adjacent to the cut has been welded due to the flat face of the catheter in the vein (first vessel) being larger than the cutting wire element. The heat from the cutting wire element is also preferably spread over this area by a conductive material that can be above, below or within the element. This creates a temperature gradient, which is a particularly advantageous feature of the present invention.

Figure 10:
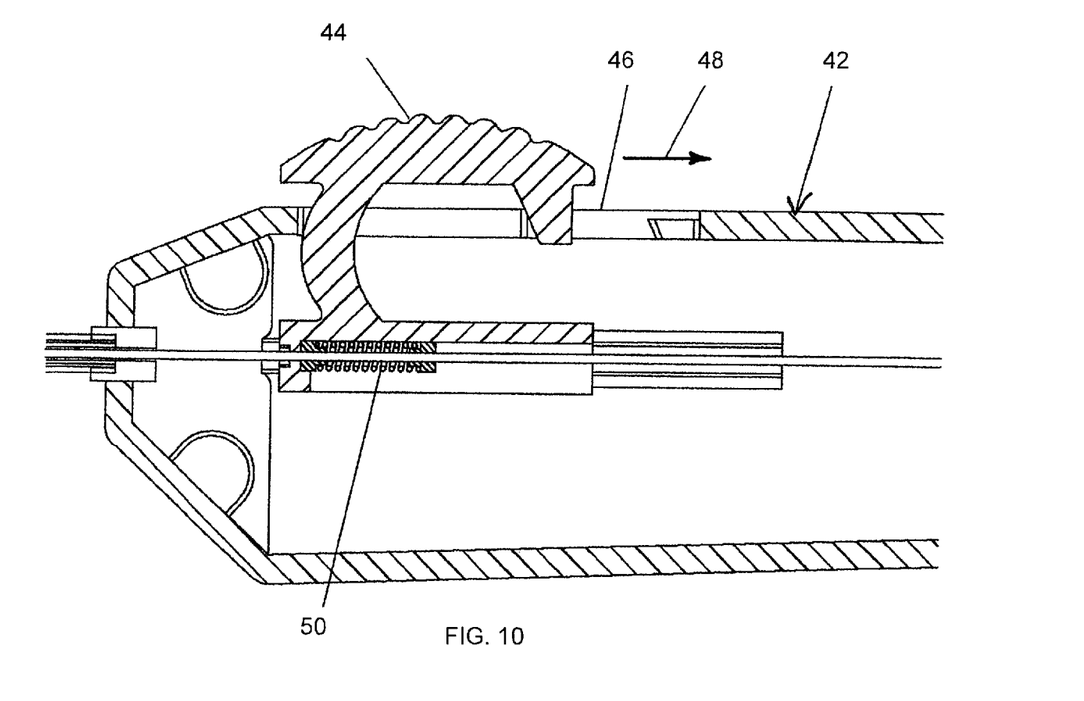
FIG. 10 is a cross-sectional view of a handle portion of the embodiment shown in FIG. 1.

FIG. 10 is a cross-sectional view of the handle portion 42 of the embodiment shown in FIG. 1. This is one possible approach for actuating the extension and retraction of the distal tip 518 relative to the elongate outer tube 512 as discussed above, though many other suitable configurations may be used alternatively. A trigger 44 is slidably disposed on the handle 42, slidable distally through a slot 46 in the direction of arrow 48, and then retractable in the reverse direction. A spring 50 within the handle controls pressure, and a locking mechanism functions to lock the trigger in the retracted state.

What is claimed is:

1. A method of creating an AV fistula between adjacent first and second vessels, comprising:
    inserting a guidewire from the first vessel into the second vessel;
    inserting a catheter comprising a proximal member and a distal member over the guidewire such that a distal tip of the distal member comes into contact with a selected anastomosis site;
    advancing the distal member into the second vessel until a distal face of the proximal member contacts a tissue wall of the first vessel so that the proximal member remains in the first vessel thereby enlarging an aperture between the two vessels;
    moving the distal member and the proximal member together to clamp tissue surrounding the aperture between the distal face of the proximal member and a proximal face on the distal member;

applying energy to an active heating member on the proximal member to cut and form the aperture, and to weld the edges thereof in order to create a desired fistula between the two vessels; and using a passive heating member disposed on the distal member to create a heating gradient across a tissue contacting surface of the distal member.

2. The method as recited in claim 1, wherein energy is directly applied to only the active heating member.

3. The method as recited in claim 1, further comprising maintaining a temperature of 150-300° C. at the location where the aperture is being cut, during the applying energy step.

4. The method as recited in claim 3, wherein the applying energy step is sustained for about 1-30 seconds to weld the walls of the two vessels together.

5. The method as recited in claim 1, wherein the moving and clamping step further comprises applying a known, controlled pressure between the distal face on the proximal member and the proximal face on the distal member, wherein the known, controlled pressure is within a range of approximately 100 mN/mm2 to 400 nN/mm2.

6. The method as recited in claim 1, further comprising rotating the distal member during the advancing step to reduce frictional resistance to the distal member.

7. The method as recited in claim 1, further comprising retaining cut tissue using structure associated with the active heating member.

8. The method as recited in claim 7, wherein the structure includes a cavity.

9. The method as recited in claim 8, wherein the structure further comprises a plurality of protruding elements extending from at least one of the distal face of the proximal member and the proximal face on the distal member and surrounding the cavity.

10. The method as recited in claim 1, wherein the active heating member is energized by DC resistive energy, and the passive heating member acts as a passive heat conductive surface to promote heat transfer through a tissue interface from the active heating member to the passive heating member.

* * * * *